United States Patent [19]
Case

[11] Patent Number: 5,351,381
[45] Date of Patent: Oct. 4, 1994

[54] DEVICE FOR REMOVING A HYPODERMIC NEEDLE FROM A SYRINGE BODY AND FOR DISTORTING THE HYPODERMIC NEEDLE

[76] Inventor: Scott A. Case, 199 Spruce Ave., Fox Lake, Ill. 60020

[21] Appl. No.: 57,679

[22] Filed: May 5, 1993

[51] Int. Cl.⁵ .................. B23Q 7/04; B26D 7/01; B23P 19/02
[52] U.S. Cl. .................. 29/283.5; 29/282; 29/426.4; 29/722; 29/777; 83/944
[58] Field of Search .................. 29/240, 240.5, 267, 29/270, 426.2, 426.4, 426.5, 720, 721, 722, 777, 6.1, 234, 278, 282, 283, 283.5, 566.1; 83/167, 994

[56] References Cited

U.S. PATENT DOCUMENTS

| | | | |
|---|---|---|---|
| 3,404,593 | 7/1966 | Arcarese et al. | 83/944 X |
| 3,683,733 | 8/1972 | Johan et al. | 83/944 X |
| 3,785,233 | 1/1974 | Robinson | 83/167 |
| 3,800,644 | 4/1974 | Garvis et al. | 83/944 X |
| 4,255,996 | 3/1981 | Choksi et al. | 83/167 X |
| 4,275,628 | 6/1981 | Greenhouse | 83/167 |
| 4,332,323 | 1/1982 | Reenstierna | 83/944 X |
| 4,404,881 | 9/1983 | Hanifl | 83/167 |
| 4,531,437 | 7/1985 | Szablak et al. | 83/167 X |
| 4,649,607 | 3/1987 | Kuhn, II | 29/6.1 |
| 4,807,344 | 2/1989 | Kelson et al. | 29/240 |
| 4,969,379 | 11/1990 | Taylor et al. | 83/167 |
| 5,091,621 | 2/1992 | Butler | 83/944 X |
| 5,138,124 | 8/1992 | Kirk et al. | 83/944 X |
| 5,138,125 | 8/1992 | Salesses | 83/944 X |

FOREIGN PATENT DOCUMENTS

| | | | |
|---|---|---|---|
| 39403 | 5/1965 | Fed. Rep. of Germany | 29/6.1 |
| 7844 | of 1895 | United Kingdom | 29/6.1 |

*Primary Examiner*—Peter Dungba Vo
*Attorney, Agent, or Firm*—Thomas R. Vigil

[57] ABSTRACT

The device for removing a hypodermic needle from a syringe body and for simultaneously distorting the hypodermic needle comprises a receptacle, a guiding structure for guiding the hypodermic needle into the receptacle, a mechanism for engaging, pulling and simultaneously distorting the hypodermic needle adjacent to the guiding structure and a mechanism for operating the engaging, pulling and distorting mechanism to pull the needle into the receptacle, the guiding structure includes an abutment for preventing the syringe body from entering the receptacle and the mechanism for engaging, pulling and distorting the needle includes a pair of intermeshing gears.

11 Claims, 5 Drawing Sheets

DEVICE FOR REMOVING A HYPODERMIC NEEDLE FROM A SYRINGE BODY AND FOR DISTORTING THE HYPODERMIC NEEDLE

BACKGROUND OF THE INVENTION

1. Field of the Invention

The present invention relates to a device for removing hypodermic needles from syringes and for distorting the hypodermic needles to provide an effective and safe means of discarding used hypodermic needles.

2. Description of the related art including information disclosed under 37 CFR §§ 1.97-1.99

Heretofore, a number of devices have been proposed for safely and effectively destroying hypodermic needles rendering them incapable of a second use. Examples of some of these devices are disclosed in the following U.S. Patents:

| U.S. Pat. No. | Patentee |
| --- | --- |
| 5,138,125 | Salesses |
| 5,138,124 | Kirk et al. |
| 4,969,379 | Taylor et al. |
| 4,531,437 | Szablak et al. |
| 4,404,881 | Hanifl |
| 4,332,323 | Reenstierna |
| 4,275,628 | Greenhouse |
| 4,255,996 | Choksi et al. |
| 3,800,644 | Garvis et al. |
| 3,785,233 | Robinson |
| 3,683,733 | Johan et al. |
| 3,404,593 | Arcarese et al. |

The Salesses U.S. Pat. No. 5,138,125 discloses an electrical needle destruction device. The device has a receiver assembly, pivotally connected to the housing. The receiver assembly includes a support arm with an opening and an open channel. When the receiver assembly is in an initial vertical position, a needle is inserted through the opening into the open channel. The receiver assembly is rotated to a second position whereby the needle is brought into contact with electrodes causing the needle to be destroyed. The support arm also has a plunger near the opening extending through a passageway which is perpendicular to the open channel. When a downward force is applied to the plunger the needle hub is immobilized. While the hub is immobilized, the syringe may then be detached from the hub.

The Kirk et al. U.S. Pat. No. 5,138,124 discloses an apparatus for destroying hypodermic needles. The housing of the device has a guide member for guiding the hypodermic needle into contact with a stationary electrode element and a rotating electrode wheel. When the needle contacts both the electrode wheel and the electrode element a circuit is completed which causes the needle to immediately become heated to a temperature greater than the needle's melting point. The needle is turned into powdered debris which falls into a compartment of the container.

The Taylor et al. U.S. Pat. No. 4,969,379 discloses a disposable needle and syringe destructor unit. The unit has an aperture for receiving the entire syringe. The syringe sits horizontally inside the unit on a V-shaped stop member which accurately positions the syringe under a piston. The piston is then brought down upon the syringe, forcing the syringe into contact with the cutting dyes. The syringe is cut into pieces which fall to the bottom of the container. When the container is full, the entire unit can be disposed of.

The Szablak et al. U.S. Pat. No. 4,531,437 discloses a rotary needle and syringe destructor. This device has a base housing and an upper closure body. The housing has an open side to receive a receptacle which collects the severed needles. The receptacle is automatically locked in a closed position upon removal from the housing. The upper body has a rotary die member for severing the needles and syringes. The rotary die member has an outer die sleeve and an inner die core. The sleeve and core have registered openings at the top to accept the needle and the hub of the syringe. The sleeve and the core also have smaller registered openings at the bottom to allow only the needle to pass through. The core is then rotated, causing the die and core openings to become misaligned and thus severing the needle from the hub and the hub from the syringe. The severed needle and hub fall into a receptacle, which when full can be removed, discarded and replaced.

The Hanifl U.S. Pat. No. 4,404,881 discloses a needle and syringe destroyer. The device has a receptacle and a base mounted on the receptacle. The base includes a shearing means and a disposal means. The shearing means has a pair of guillotine shears each having a movable shear blade. Static shear blades having apertures for syringe and needle entry are also mounted on the base. The needle is positioned within the apertures. The movable shear blades are then activated by a hand manipulable lever, bringing the movable blades into contact with the needle close to cutting edges of the fixed blades, and thus severing the needle. The severed portions of the needle fall directly into the receptacle. Remaining portions of the syringe barrel may be deposited in the disposal means which is located on the receptacle and comprises an opening and a movable closure lid.

The Reenstierna U.S. Pat. No. 4,332,323 discloses a destruction device for injection needles. The destruction device has an outer sleeve with a bottom and a concentric inner sleeve. Blades are fixedly attached to the inner surface of the outer sleeve and are pivotally retained by the inner sleeve. When a needle is inserted into the device for destruction, the needle sits within the inner sleeve. The assembly is then struck or pressed against some object at the bottom, forcing the outer sleeve towards the inner sleeve and forcing the blades to pivot and engage the needle, thus bending or breaking the needle.

The Greenhouse U.S. Pat. No. 4,275,628 discloses a syringe and needle destroyer. This needle destroyer has a horizontally movable severing means having an upper blade and a lower blade. The blades are moved horizontally when a lever is actuated. The needle and hub portion of the syringe are inserted into an opening on top of a cover of a receptacle. When the lever is actuated the blades move horizontally, and the lower blade severs the needle from the hub while the upper blade severs the hub from the syringe. The severed needle and hub then fall into the bottom of the receptacle.

The Choksi et al. U.S. Pat. No. 4,255,996 discloses a needle destroyer with an improved mechanical advantage. The device has a separable housing having a top portion and a bottom portion. An opening in the top portion is provided to accept the needle and hub. Hub and cannula cutters laterally slide relative to the hub center and simultaneously sever both the hub and the cannula in one motion. The mechanical advantage to the cannula cutter is provided by joining the hub and cannula cutters at a slidable joint and by providing non-coaxial pivot points for the cutters. The severed hub and cannula fall into a box located in the bottom portion of the housing.

The Garvis et al. U.S. Pat. No. 3,800,644 discloses a destruction and disposal device for hypodermic syringes. A syringe or multiple syringes are placed in the feeding tray. The syringes are automatically, one by one, fed into a cutting section of the device. The cutting section has a plurality of cutting blades having a fixed set of blades and a movable set of blades. The movable set is capable of moving into and out of a shearing relationship with the fixed set. The movable blades are then actuated, cutting the syringe into a plurality of pieces. The pieces are then dispensed into a collection bin located beneath the cutting section. The entire process of feeding, cutting and dispensing is controlled by a motor control unit of the device.

The Robinson U.S. Pat. No. 3,785,233 discloses a cutting punch for destroying hypodermic syringes. The punch comprises a base, a standard extending from the base and an overhang portion over the base. The base is fitted with a die retainer having a cutter with a groove at the front and the rear. The grooves are of semi-cylindrical shape and serve to support the hypodermic syringe in a substantially position when inserted into the die. The overhang portion is bored with a cylindrical passage to accommodate a plunger having cutting edges. The plunger is pressed downwardly to effect the cutting operation, thus severing the needle and the hub of the syringe. The severed portions fall into a drawer positioned below the base.

The Johan et al. U.S. Pat. No. 3,683,733 discloses an apparatus for destroying hypodermic needles. The device has a rotatable cylindrical inner cutting body having a bore. The inner body is positioned within a stationary outer cutting body which cooperates with the inner body and has a bore with sharp cutting surfaces. In the initial position the two bores are aligned. A needle is inserted through the bores of the inner and outer bodies. The inner bore is then rotated so that the needle is severed along the cutting surfaces of the outer body.

The Arcarese et al. U.S. Pat. No. 3,404,593 discloses a hypodermic syringe destroyer having a cabinet with a removable container. A cutting means is provided comprising a housing which is located on top of the container having two axially aligned apertures, a movable member with a handle and a pair of arms, and shearing elements attached to the arms of the movable member. The hypodermic syringe is inserted into the housing and through the apertures, then the handle is operated so as to bring the shearing elements into contact with the syringe, thus severing the syringe. The severed portions of the syringe then fall into the removable container.

SUMMARY OF THE INVENTION

According to the present invention there is provided a device for removing a hypodermic needle from a syringe body and for simultaneously distorting the hypodermic needle. The device comprises a receptacle, a guiding structure for guiding the hypodermic needle into the receptacle, a mechanism for engaging, pulling and simultaneously distorting the hypodermic needle adjacent to the guiding structure and a mechanism for operating the engaging, pulling and distorting mechanism to pull the needle into the receptacle.

The guiding structure includes an abutment for preventing the syringe body from entering the receptacle. The mechanism for engaging, pulling and distorting the needle includes a pair of intermeshing gears.

DESCRIPTION OF PREFERRED EMBODIMENTS

While the hypodermic needle removal and distortion device of the present invention is susceptible of several constructions, there is shown in FIGS. 1-9 several preferred embodiments of such a device constructed according to the teachings of the present invention, with the understanding that the present disclosure is not intended to be limited to the specific constructions thereof illustrated in the drawings.

Illustrated in FIGS. 1-4, is one embodiment of the hypodermic needle removal and distortion device 10.

Figure 1:
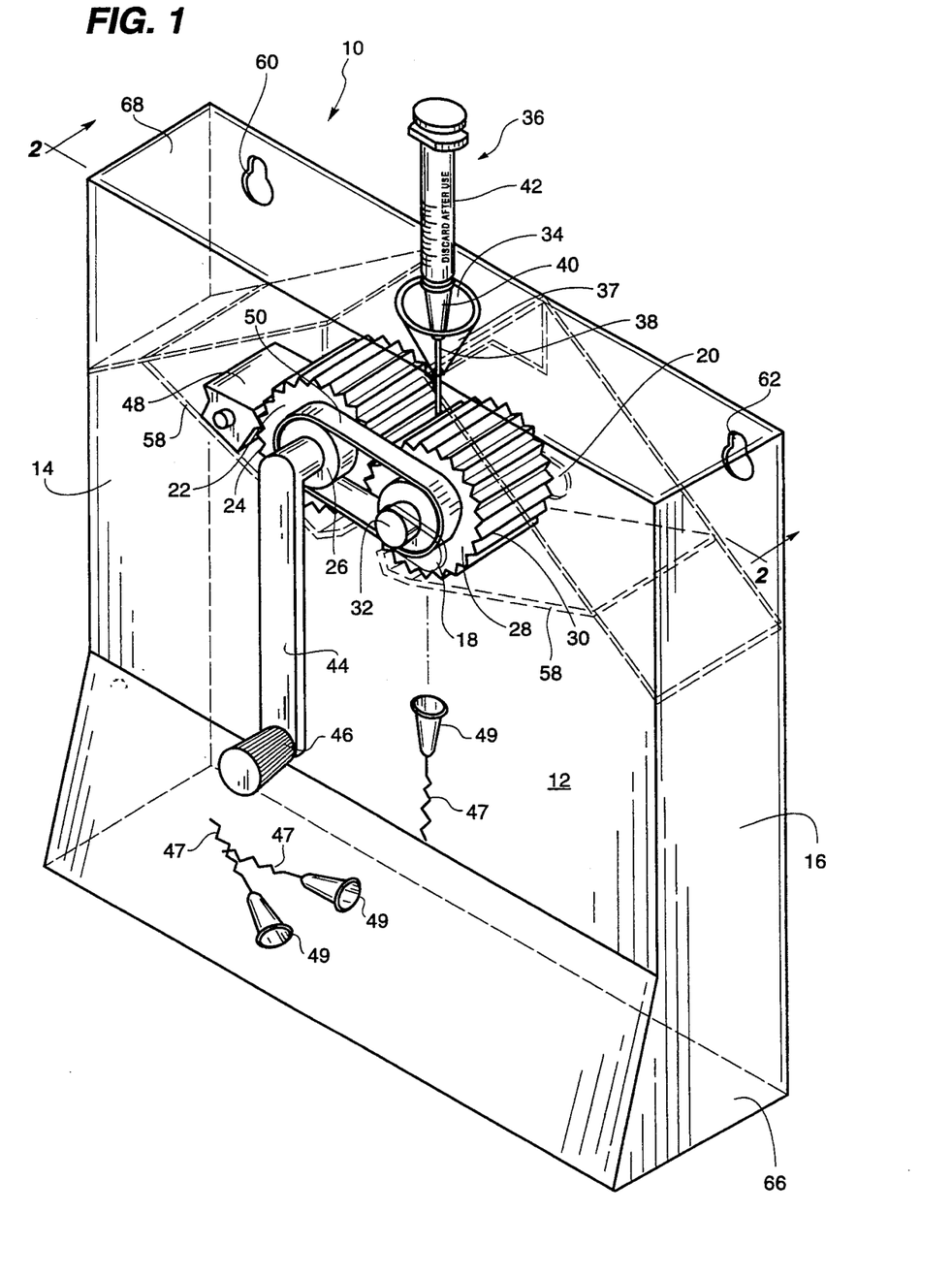
FIG. 1 is a perspective view of one embodiment of a device constructed according to the teaching of the present invention for removing a hypodermic needle from a syringe body and for simultaneously distorting the hypodermic needle.

In this embodiment, as can be seen in FIG. 1, the device 10 includes a receptacle 12 with a front wall 14 and a rear wall 16, and, if desired, can be made of transparent or translucent plastic. The front wall 14 and the rear wall 16 have aligned slots 18 and 20. The receptacle 12 also has mounted therein a first gear 22 with teeth 24. The first gear 22 is mounted on a first axle 26 which extends from the front wall 14 to the rear wall 16. The receptacle 12 also has a second gear 28 with teeth 30, mounted on a second axle 32 which also extends from the front wall 14 to the rear wall 16.

In an at rest position, the second axle 32 is parallel to the first axle 26 and is spaced from the first axle 26 a small distance sufficient to enable the teeth 24 and 30 of the gears 22 and 28 to mesh continuously as the gears 22 and 28 are rotated.

The receptacle 12 also has an opening 34. When a hypodermic syringe 36 is inserted into the opening 34 of the receptacle 12, the syringe 36 is guided by a funnel shaped feed tube 37 toward the area of intermeshing of the gears 22 and 28. The hypodermic syringe 36 comprises three parts, a needle 38, a hub 40 and a syringe body 42. The needle 38 and hub 40 are integrally formed and usually do not become separated during operation of the device 10. The hub 40 and syringe body 42 however do become separated upon operation of the device 10.

Figure 2:
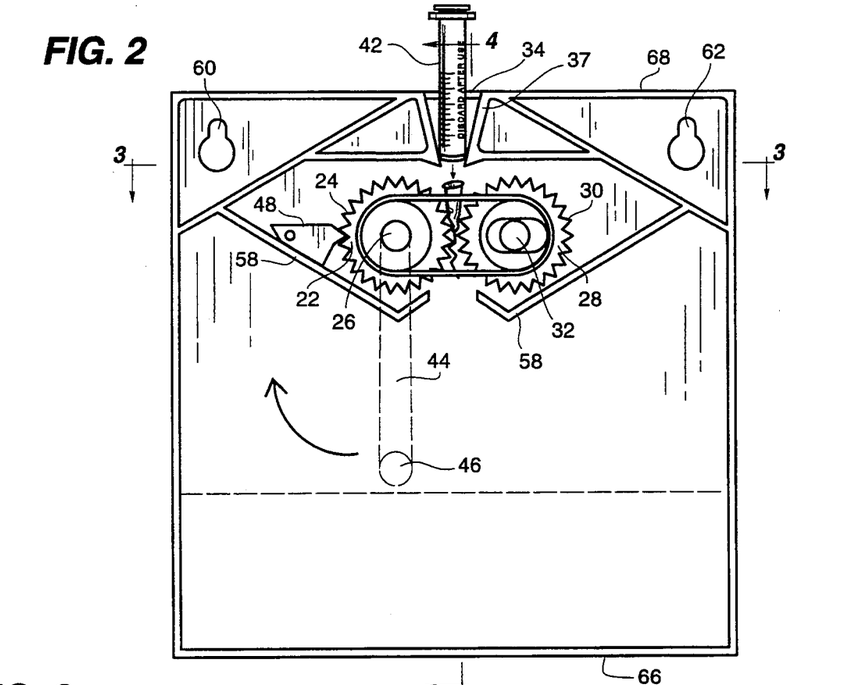
FIG. 2 is a side to side vertical sectional view of the device shown in FIG. 1 and is taken along line 2—2 in FIG. 1.

Upon operation of the device 10 as shown in FIG. 2, the gears 22 and 28 are rotated by a lever 44 attached to the first axle 26. When the free end 46 of the lever 44 is turned in a clockwise direction, the first gear 22 also turns in a clockwise direction, which then drives the second gear 28 in a counter-clockwise direction. The first gear 22 is prevented from turning in a counter-clockwise direction by a ratchet 48 mounted in the receptacle 12, which engages the teeth 24 of the first gear 22 allowing rotation in the clockwise direction, but preventing rotation in the counter-clockwise direction.

As the gears 22 and 28 are rotated in the allowable directions, the needle 38 is gripped by the gears 22 and 28 and pulled downward. The hub 40 is also pulled downward. The needle 38 and the hub 40 are pulled off of the syringe body 42 as the gears 22 and 28 pull the needle 38 and hub 40 downward. As the needle 38 passes between the meshed teeth 24 and 30 of the gears 22 and 28, the needle 38 becomes permanently distorted to a zig zag or undulating shape to render impossible a second use of the needle 38.

In FIG. 1, the needle 47 is shown distorted into a zig-zag shape which is an outline form of the intermeshing teeth 24 and 30.

The hub 40 is made of a resilient material and has a larger diameter than the needle 38. Therefore, as shown in FIG. 2, as the hub 40 passes between the teeth 24 and 30 of the gears 22 and 28, the second gear 28 and the second axle 32 are moved horizontally along the slots 18 and 20 to a second position. The horizontal movement makes turning of the lever 44 easier on the operator as the hub 40 passes between the gears 22 and 28. After the hub 40 has passed between the gears 22 and 28, the distorted needle 47 and hub 49 fall to the bottom of the receptacle 12.

A tensioning mechanism, such as rubber bands 50 and 52, are used to pull the second axle 32 back to it's at rest position. The rubber bands 50 and 52 are looped around the axles 26 and 32.

As shown in FIG. 2, the first rubber band 50 is attached around the axles 26 and 32 near the front wall 14 and the second rubber band 52 is attached around the axles 26 and 32 near the rear wall 16. The rubber bands 50 and 52 may be replaced instead by springs (not shown) or any other suitable tensioning mechanism which acts on the second axle 32 to hold the second axle 32 in its at rest position, and yet is resilient enough to allow the second gear 28 to move to the second position as the hub 40 passes between the gears 22 and 28 and can then force the second gear 28 to its original position after the hub 40 has passed between the gears 22 and 28.

After the removal and distortion of the needle 38 and hub 40, the syringe body 42 is still positioned within the funnel shaped feed tube 37. The syringe body 42 can then be safely discarded by being thrown in the standard bio-hazard container. The diameter of the feed tube 37 at the bottom is smaller than the diameter of the syringe body 42. The syringe body 42 butts against the conical wall of the funnel shaped feed tube 37 and is prevented thereby from being pulled into the receptacle 12. The needle 38 and hub 40 however are able to enter the receptacle 12. The needle 38 and the hub 40 are gripped and pulled by the gears 22 and 28 and become detached from the syringe body 42. When some downward force exists on the needle 38 from the gears 22 and 28 gripping the needle 38, prior to the hub 40 separating from the syringe body 42, a seal is formed between the syringe body 42 and the upper surface of the interior feed tube 37 wall preventing any material or fluid from spraying out of the receptacle 12. A flap (not shown) ALSO may be attached over the opening 34 of the receptacle 12 to further prevent any material from spraying out of the receptacle 12.

In order to prevent distorted needles 47 and hubs 49 from interfering with the operation of the gears 22 and 28, baffles 58 are located in the receptacle 12 positioned below the gears 22 and 28 as shown in FIGS. 1 and 2. The baffles 58 also help ensure that distorted needles 47 and hubs 49 will not be able to exit the receptacle 12 via the opening 34 by preventing the distorted needles 47 and hubs 49 from even reaching the opening 34.

The device 10 may be wall mountable or may be a stand alone unit. To make the device 10 wall mountable, keyhole slots 60 and 62 can be cut out of the rear wall 16 of the receptacle 12 as shown in FIGS. 1 and 2. Screw heads mounted in a wall (not shown) can be inserted into the keyhole slots 60 and 62. Gravity keeps the device 10 from becoming unmounted from the screw heads unless an upward force is applied to the receptacle 12 to lift the device 10 off of the screw heads.

Figures 3, 4:
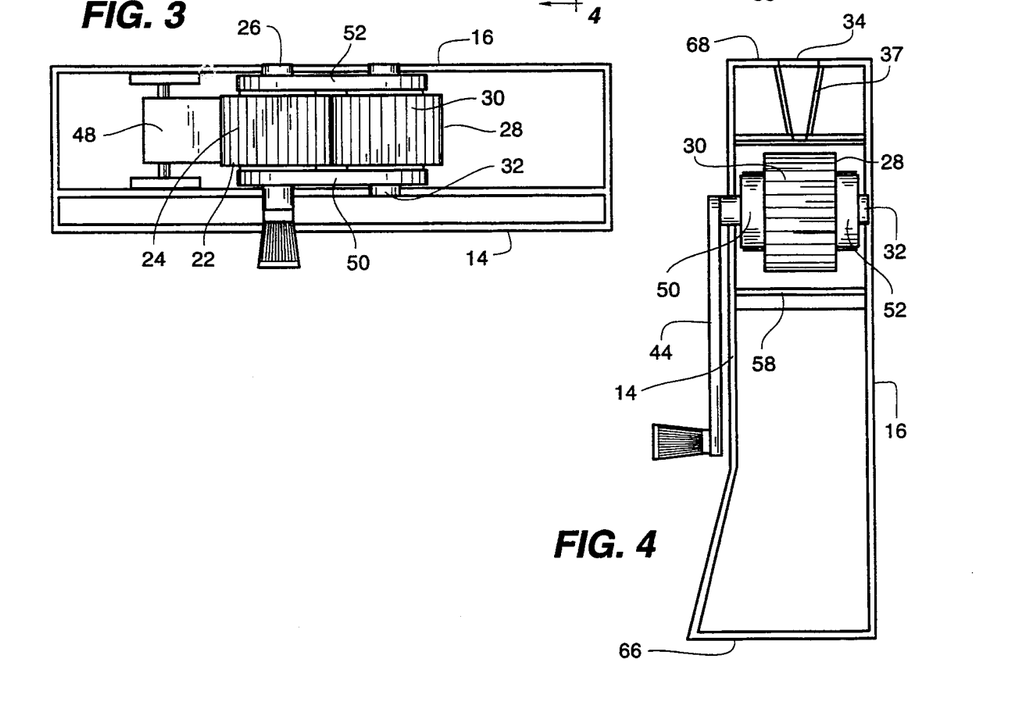
FIG. 3 is a horizontal sectional view of the device shown in FIG. 2 and is taken along line 3—3 of FIG. 2.
FIG. 4 is a front to back vertical sectional view of the device shown in FIG. 2 and is taken along line 4—4 in FIG. 2.

For the device 10 to be stand alone, the bottom side 66 of the receptacle 12 is made wider than the top side 68, forming a base, as shown in FIG. 4. This provides stability to the device 10 as the device 10 rests on a surface such as a table.

The receptacle 12 is sealed and made of plastic and is inexpensive enough so that the entire device 10 may be discarded when the device 10 becomes full of destroyed needles 47 and hubs 49. Because the receptacle 12 is sealed, accidental opening of the device 10 and injury from the distorted needles 47 is prevented. The device 10 is economical because only distorted needles 47 and hubs 49 are stored within the receptacle 12, thus the receptacle 12 fills more slowly than previous needle destruction devices which also contain the discarded syringe body 42.

The receptacle 12 can be made of a translucent plastic or have a vertical translucent strip (not shown) so that the operator can see when the receptacle 12 is full.

Figure 5:
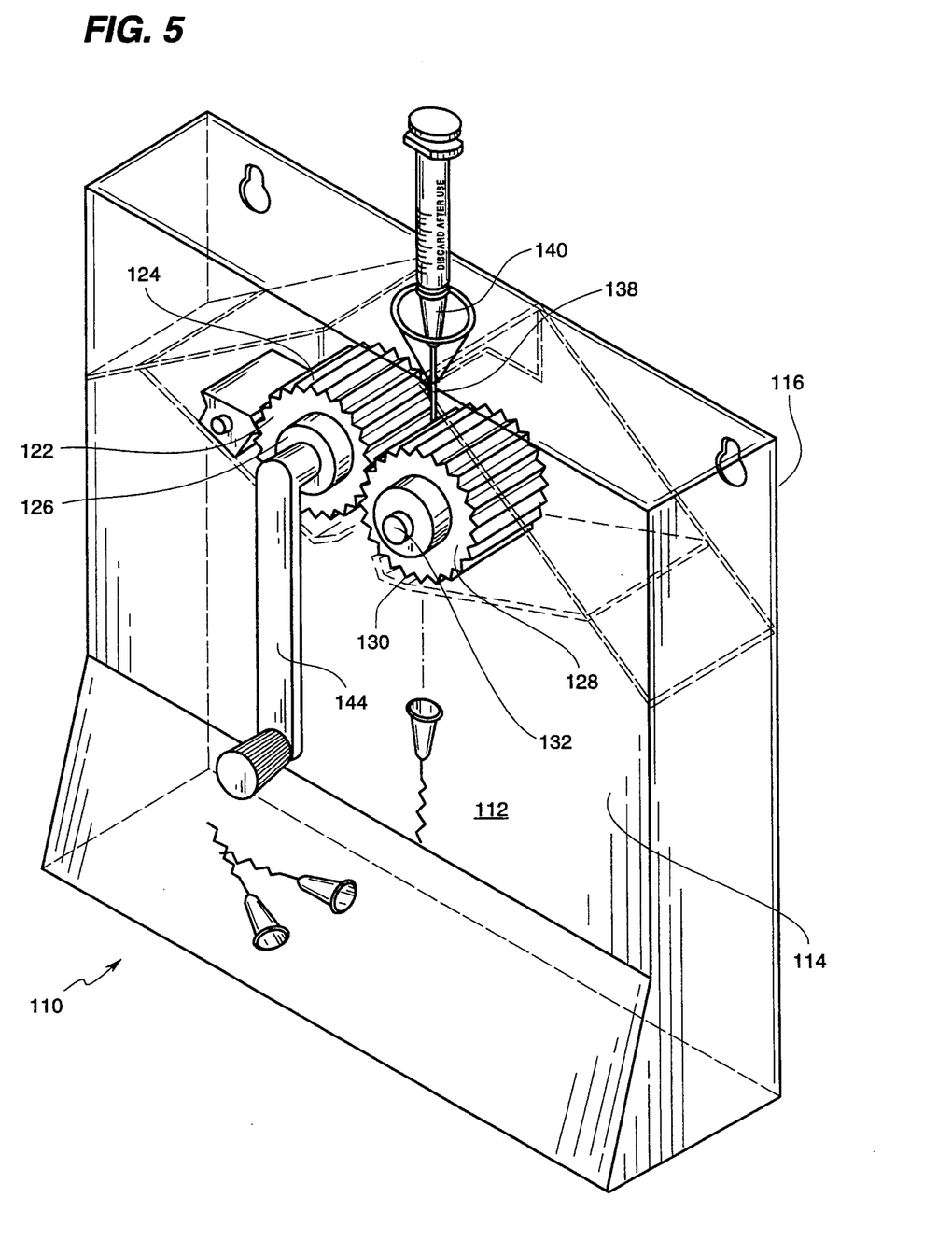
FIG. 5 is a perspective view of another embodiment of a device constructed according to the teachings of the present invention.

In another embodiment of the invention shown in FIG. 5, a device 110 includes a receptacle 112 having a front wall 114 gears 122 and 128 and axles 126 and 132 which are made entirely of plastic. In this embodiment, the need for the aligned slots 18 and 20 of FIGS. 1 and 2, is eliminated. The axles 126 and 132 are simply mounted between the front and rear walls 114 and 116 of the receptacle 112 positioned such that the teeth 124 and 130 of the gears 122 and 128 mesh. Due to the strong yet resilient and flexible nature of the plastic, a needle 138 is distorted in the same manner as in FIG. 2. However as a hub of a syringe 140 passes between the gears 122 and 128, slight flexing of the plastic gears 122 and 128 and the axles 126 and 132 occurs, as the lever 144 is rotated. Then, after the hub 140 has passed between the gears, the gears 122 and 128 and axles 126 and 132 return to their original shapes and positions, ready to accept another needle 138 and hub 140.

Illustrated in FIGS. 6–9 is a motorized version of a hypodermic needle removal and destruction device 200

(FIGS. 8 and 9) constructed according to the teachings of the present invention.

Figure 6:
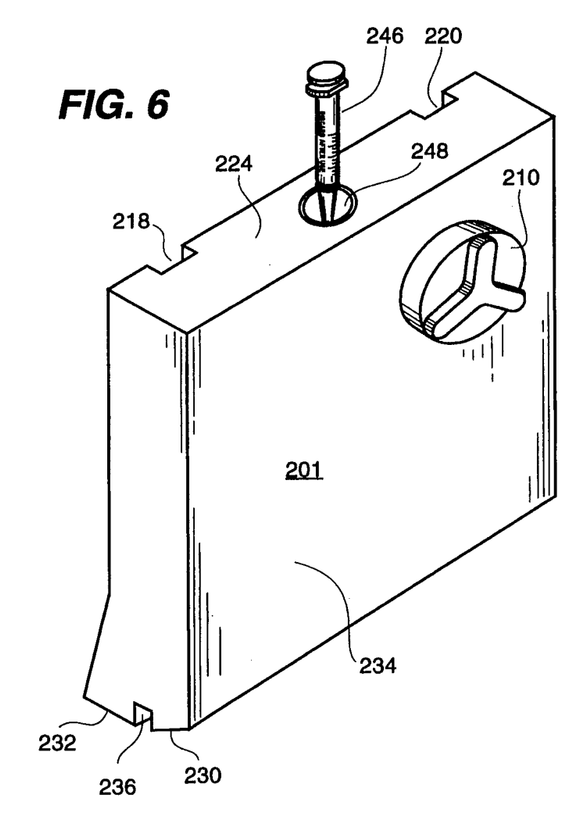
FIG. 6 is a perspective view of a receptacle unit of a motorized device constructed according to the teachings of the present invention.
Figure 7:
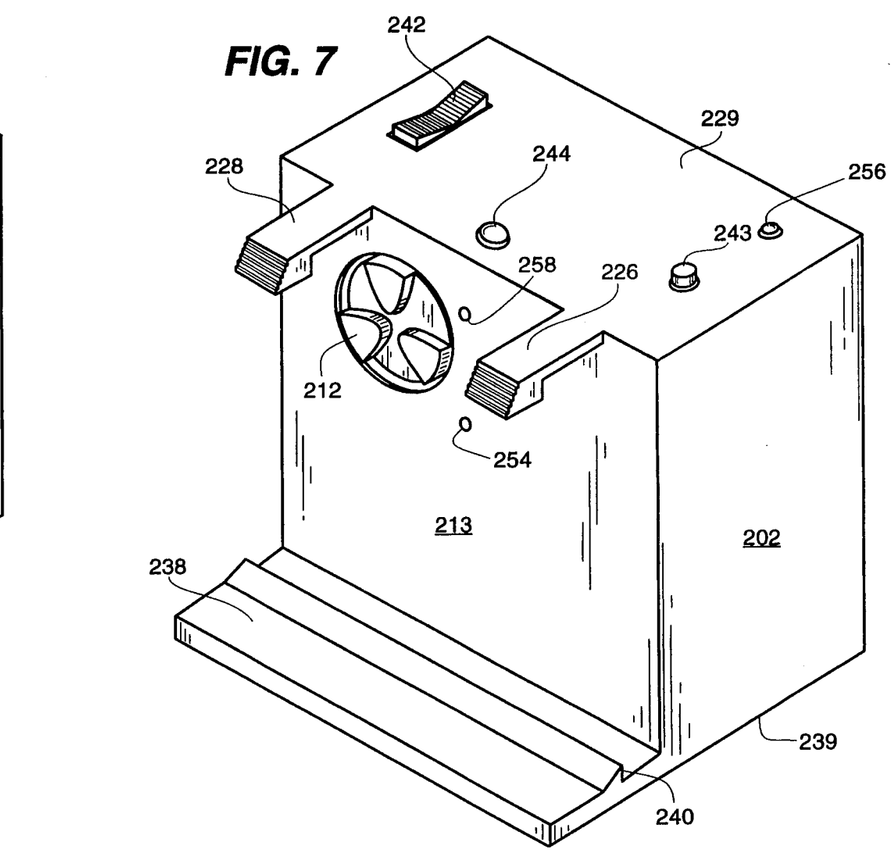
FIG. 7 is a perspective view of a motor drive unit of the motorized device constructed according to the teachings of the present invention.

The device 200 of this embodiment comprises a receptacle unit 201 shown in FIG. 6 and a motor drive unit 202 shown in FIG. 7. The receptacle unit 201 is similar to the receptacles 12 and 112 shown in FIGS. 1 and 5. However, the receptacle unit 201 has been adapted to be used with the motor drive unit 202. The motor drive unit 202 replaces the lever 44 of FIG. 1.

An external first coupling gear 210 is mounted on a shaft (not shown) which extends from a housing of the receptacle unit and on which a gear, like gear 22, is mounted within the receptacle unit 201. This gear is adapted to mate with a second coupling gear 212 recessed in a housing wall 213 of the motor drive unit 202. The second coupling gear 212 is driven by a motor 216, shown in FIG. 9, such as a 110 volt, low rpm, high torque, uni-directional motor located within the motor drive unit 202.

The receptacle unit 201 shown has spaced apart notches 218 and 220 at the intersection of a front wall 222 and a top wall 224 of a housing of the receptacle unit 201 so that fingers 226 and 228 spaced apart along the upper margin of the wall 213 of the motor drive unit and protruding forwardly therefrom between, can snap into the notches 218 and 220, respectively, and hold the receptacle unit 201 and motor drive unit 202 coupled together with the coupling gears 210 and 212 in coupling engagement operation of the motor drive unit 202. The receptacle unit 201 has a rear, lower inclined bottom surface 230 and a forward bottom surface 232. The surface 230 inclines downwardly from a back wall 234 of the housing of the receptacle unit 201 to a transversely extending groove 236 running along the bottom wall of the receptacle unit 201. The groove 236 ensure easy and proper positioning between the receptacle unit 201 and motor drive unit 202 when mated.

The motor drive unit 202 has a bottom surface 239 and a forward base portion 238 extending from the bottom margin of the wall 213. The base portion 238 supports the receptacle unit 201 in the mated position. A tapered lip 240 is provided on the base portion 238 to ensure that the receptacle unit 201 locks into place when mated with the motor drive unit 202. The fingers 226 and 228 are able to flex upward to allow insertion and removal of the receptacle unit 201 from the mated position with the motor drive unit 202 as shown in FIGS. 8 and 9 when the receptacle unit 201 is moved into engagement with the motor drive unit 202.

The motor drive unit 202 also has a main power on/-off switch 242, a momentary push button switch 243 and an LED "on" lamp 244 located on the top wall 229. The LED "on" light 244 indicates whether or not the motorized unit 202 has main power and can be activated by pushing the switch 243.

Figure 9:
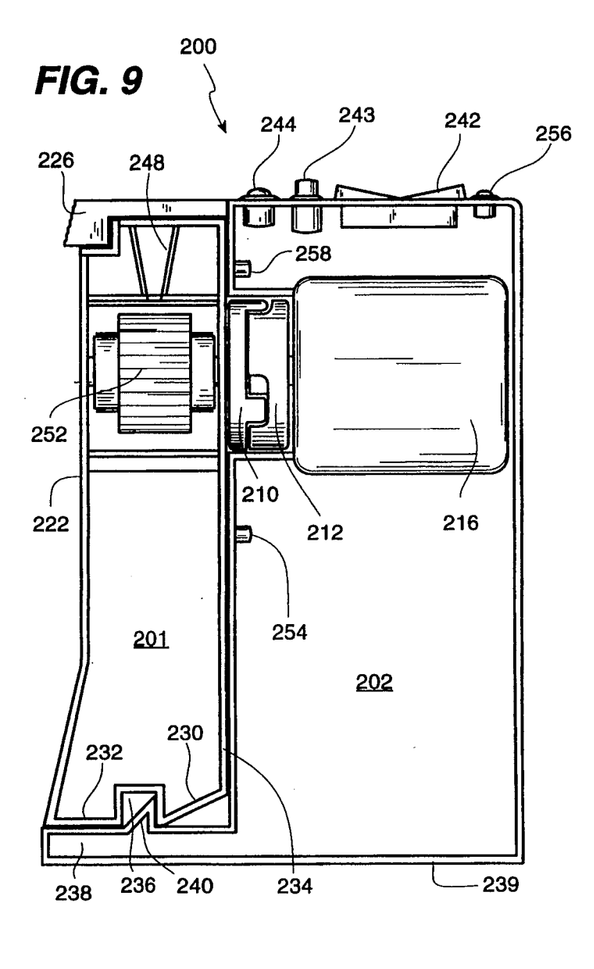
FIG. 9 is a vertical sectional view of the motorized version of the device shown in FIG. 8 and is taken along line 9—9 of FIG. 8.

The momentary push button 243 is pushed by a person after a syringe 246 has been placed in an opening 247 of the receptacle unit 202 at the top of a conical wall 248 (FIG. 9). The motor 216 is then activated for a period of time sufficient to pull a needle (not shown) off the syringe 246 between a first gear (not shown) and a second gear 252 and is distorted and destroyed. The motor 216 shuts off automatically after a set period of time.

Figure 8:
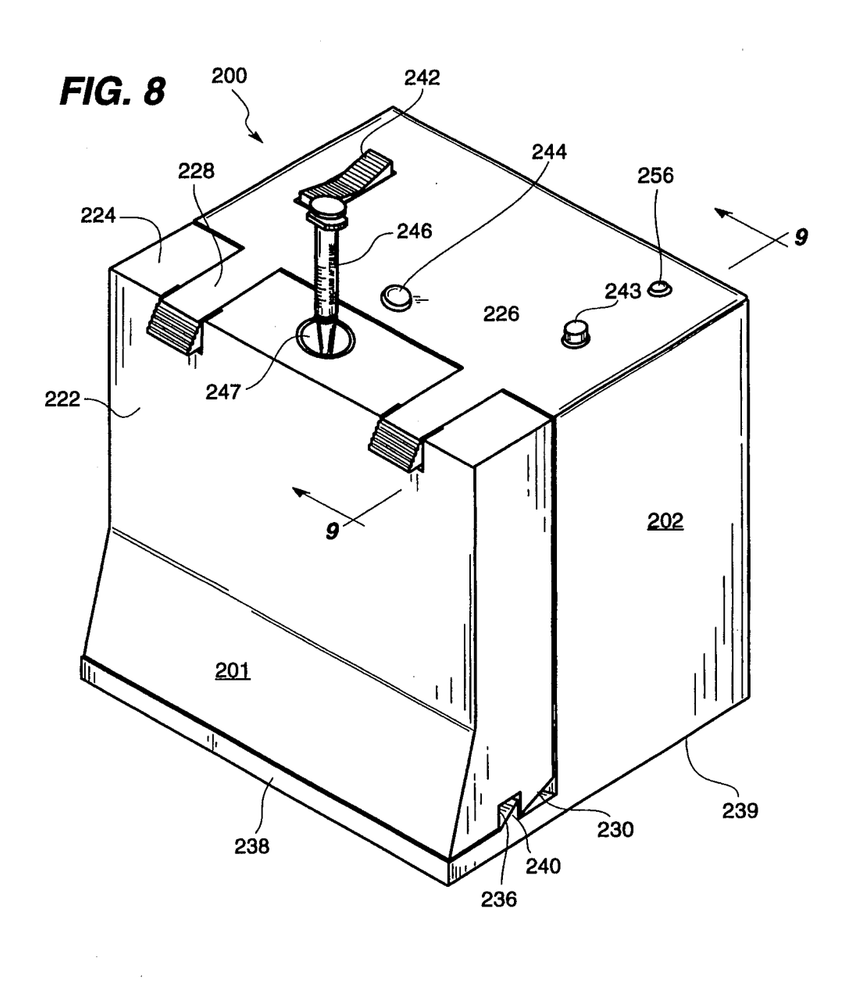
FIG. 8 is a perspective view of the device showing the receptacle unit and the motorized unit in mating relationship.

When the receptacle unit 201 and motor drive unit 202 are mated as shown in FIGS. 8 and 9, the second coupling gear 212 of the motor drive unit 202 and the first coupling gear 210 of the receptacle unit 201 are mated such that when the motor 216 is activated, turning the second coupling gear 212, the second coupling gear 212 then drives the first coupling gear 210, which in turn causes the second gear 252 to be driven and in intermeshing engagement with the first gear.

Note, that as shown in FIGS. 8 and 9 when the receptacle unit 201 and the motor drive unit 202 are in the proper mated position: 1) the fingers 226 and 228 of the motor drive unit 202 lock into the notches 218 and 220 of the receptacle unit 201; 2) the lip 240 on the base portion 238 of the motor drive unit 202 is received into the groove 236 on the bottom of the receptacle unit 201; and, 3) the first coupling gear 210 and the second coupling gear 212 are in meshing engagement.

The motor drive unit 202 is also shown having a first proximity sensor 254. The first proximity sensor 254 is coupled to a "receptacle-full" indicating LED 256 and to the motor 216 power supply circuit (not shown). When the first proximity sensor 254 detects the presence of distorted needles at a certain level, the LED 256 will be energized and the light emitted indicates that the receptacle unit 201 should be replaced. At the same time, the power supply circuit is deenergized. Thus, a person can then detach the full receptacle unit 201 and connect a new empty receptacle unit 201.

The device 200 is further shown with a second proximity sensor 258 located on the receptacle unit 201. The second proximity sensor 258 can be connected to the power supply circuit for the motor 216 and used instead of the push button switch 243 to activate the device 200. In this respect the motor drive unit 202 can work automatically by sensing, with the sensor 258, the placement of a hypodermic syringe 246 in the conical wall 248 and then automatically energize the motor 216. The second proximity detector 258 is coupled to the motor 216 power supply circuit in the motor drive unit 202 and activates the motor 216 for a preset period of time when the second proximity sensor 258 detects the presence of a needle of the syringe 246 situated in the conical wall 248.

From the foregoing description, it will be understood that modifications can be made to the various embodiments of the needle removal and distortion device 10, 110 or 200 constructed according to the teachings of the present invention and described above. Also, it will be apparent that the needle removal and distortion device 10, 110 or 200 described above has a number of advantages and features, some of which have been disclosed above and others of which are inherent therein. Accordingly, the scope of the invention is only to be limited as necessitated by the accompanying claims.

I claim:

1. A device for removing a hypodermic needle and hub from a syringe body and for simultaneously distorting the hypodermic needle, said device comprising:
   a receptacle;
   a guiding structure for guiding the hypodermic needle into said receptacle;
   said guiding structure including abutment means for preventing entry of the syringe body into said receptacle;
   engaging, pulling and distorting means, mounted inside said receptacle adjacent to said guiding structure, said engaging, pulling and distorting means engaging the needle and pulling the needle and the hub away from the syringe body and into said receptacle and said engaging, pulling and distorting means simultaneously permanently distorting the hypodermic needle into a shape that makes reuse of the needle impossible;

an operating means, said operating means operating said engaging, pulling and distorting means to pull the needle and hub away from the syringe body and into said receptacle.

2. The device of claim 1 wherein said guiding structure is a funnel shaped feed tube having a top opening and a bottom opening, said bottom opening diameter being smaller than said syringe body diameter.

3. The device of claim 1 wherein said engaging, pulling and distorting means comprises:
   a first axle mounted in said receptacle;
   a first gear mounted on said first axle;
   a first set of teeth on said first gear;
   a second axle mounted in said receptacle;
   a second gear mounted on said second axle and being spaced only a small distance from said first gear;
   a second set of teeth on said second gear, said second set of teeth being in meshing engagement with said first set of teeth; and
   ratchet means, said ratchet means allowing said first gear to rotate in only one allowable direction.

4. The device of claim 3 wherein said operating means comprises:
   a lever having a free end and a fixed end, said fixed end being attached to said first axle and being adapted, upon manipulation thereof, to cause said first axle to rotate when said free end of said lever is rotated about said fixed end of said lever.

5. The device of claim 3 further including tensioning means associated with said first axle and/or said second axle for maintaining said second gear in a meshed relationship with said first gear when said first and said second gears are in an at rest position, said tensioning means allowing said second gear to move a small distance from said first gear when a hub of a syringe passes between said first and said second gears, and said tensioning means returning said second gear to the meshed relationship with said first gear after the hub has completely passed between said first and said second gear.

6. The device of claim 1 wherein said operating means comprises:
   a motor having a shaft;
   a first coupling gear attached to said motor shaft; and
   a mating, second coupling gear attached to said engaging, pulling and distorting means, said second coupling gear mating with said first coupling gear.

7. The device of claim 1 further comprising two units, one being a receptacle unit, and the other being a motor drive unit and wherein said motor drive unit includes:
   a housing;
   a motor having shaft mounted in said housing;
   a first coupling gear;
   said first coupling gear being mounted on said motor shaft; and,
   said receptacle unit having a second coupling gear connected to said engaging, pulling and operating means;
   said first coupling gear and said second coupling gear being arranged to engage each other when said receptacle unit and said motor drive unit are connected with each other whereby said motor is coupled to said engaging, pulling and operating means to operate same for removing a needle from a syringe body and permanently distorting the hypodermic needle into a shape that makes reuse of the needle impossible.

8. The device of claim 7 further including a sensor for sensing when said receptacle is full of distorted needles and an LED coupled to said sensor mounted in said motor drive unit for indicating when said receptacle sensor senses that said receptacle is full of distorted needles.

9. The device of claim 8 wherein said sensor is also coupled to a power supply circuit for said motor and when said sensor senses that said receptacle is full of distorted needled said power supply circuit is de-energized.

10. The device of claim 7 further comprising a needle sensor located in said motor unit adjacent said guiding structure;
    said needle sensor being coupled to the power supply for said motor so that, when said sensor senses a needle in said guiding structure, said motor is energized.

11. A device for removing a hypodermic needle and hub from a syringe body while simultaneously permanently distorting the hypodermic needle, said device comprising:
    a receptacle having an opening for receiving the hypodermic needle and hub;
    abutment means, said abutment means preventing entry of the syringe body into said receptacle;
    pulling means mounted inside said receptacle, said pulling means pulling the needle and the hub away from the opening, off of the syringe body, and into the receptacle; and,
    distorting means mounted inside the receptacle, said distorting means simultaneously permanently distorting the hypodermic needle into a shape that makes reuse of the needle impossible while the needle is pulled away from the opening and into the receptacle.

* * * * *